US009120086B2

(12) United States Patent
Thakur et al.

(10) Patent No.: US 9,120,086 B2
(45) Date of Patent: Sep. 1, 2015

(54) COPPER CHROMITE HYDROGENATION CATALYSTS FOR PRODUCTION OF FATTY ALCOHOLS

(76) Inventors: Deepak S. Thakur, Solon, OH (US); William J. Carrick, Chardon, OH (US)

( * ) Notice: Subject to any disclaimer, the term of this patent is extended or adjusted under 35 U.S.C. 154(b) by 708 days.

(21) Appl. No.: 13/301,917

(22) Filed: Nov. 22, 2011

(65) Prior Publication Data
US 2012/0136179 A1 May 31, 2012

Related U.S. Application Data

(60) Provisional application No. 61/418,063, filed on Nov. 30, 2010.

(51) Int. Cl.
| | |
|---|---|
| *B01J 23/02* | (2006.01) |
| *B01J 23/04* | (2006.01) |
| *B01J 23/72* | (2006.01) |
| *B01J 23/78* | (2006.01) |
| *B01J 23/86* | (2006.01) |
| *B01J 23/00* | (2006.01) |
| *B01J 21/00* | (2006.01) |
| *B01J 23/70* | (2006.01) |
| *B01J 35/10* | (2006.01) |
| *B01J 37/00* | (2006.01) |
| *B01J 37/04* | (2006.01) |
| *C07C 29/149* | (2006.01) |

(52) U.S. Cl.
CPC .............. *B01J 23/868* (2013.01); *B01J 35/108* (2013.01); *B01J 35/1014* (2013.01); *B01J 35/1038* (2013.01); *B01J 35/1042* (2013.01); *B01J 37/0009* (2013.01); *B01J 37/04* (2013.01); *C07C 29/149* (2013.01)

(58) Field of Classification Search
CPC ............ B01J 23/02; B01J 23/04; B01J 23/72; B01J 23/78; B01J 23/86
USPC ......... 502/243, 244, 250, 256, 318, 344, 345, 502/524
See application file for complete search history.

(56) References Cited

U.S. PATENT DOCUMENTS

| | | | | | |
|---|---|---|---|---|---|
| 3,216,954 | A | * | 11/1965 | Howk et al. .................... | 502/217 |
| 3,756,964 | A | * | 9/1973 | Frazee et al. ................... | 502/244 |
| 4,199,479 | A | * | 4/1980 | Wilkes .......................... | 502/174 |
| 4,310,703 | A | * | 1/1982 | Tamaru et al. ................. | 568/361 |
| 4,440,873 | A | * | 4/1984 | Miyazaki et al. .............. | 502/244 |
| 4,666,879 | A | | 5/1987 | Kelly et al. | |
| 4,855,273 | A | * | 8/1989 | Pohl et al. ...................... | 502/244 |

(Continued)

FOREIGN PATENT DOCUMENTS

| | | | | |
|---|---|---|---|---|
| EP | 0494898 B1 | | 2/1995 | |
| WO | 2012/074841 | * | 6/2012 | ............... B01J 23/86 |

*Primary Examiner* — Patricia L Hailey

(57) ABSTRACT

Provided are hydrogenation catalysts for processing esters into fatty alcohols. More particularly, the catalysts are for vapor-phase hydrogenation of methyl esters to fatty alcohols under fixed-bed conditions, where conditions are typically in a temperature range of 200 to 250° C. and a pressure range of 30 to 50 bar. Methods of making and using the same are also provided. These catalysts comprise a copper chromite, an alkali metal or alkaline earth metal component, and an inorganic matrix component, which are processed together to form the catalyst. The alkali metal component can comprise sodium (Na), potassium (K), rubidium (Rb), caesium (Cs), or combinations thereof. The alkaline earth metal can comprise magnesium (Mg), calcium (Ca), barium (Ba), or combinations thereof.

18 Claims, 1 Drawing Sheet

(56) References Cited

U.S. PATENT DOCUMENTS

| | | |
|---|---|---|
| 5,030,609 A | 7/1991 | Turner et al. |
| 5,043,485 A | 8/1991 | Fleckenstein et al. |
| 5,124,295 A | 6/1992 | Nebesh et al. |
| 5,217,937 A * | 6/1993 | Schneider et al. ............ 502/242 |
| 5,294,583 A * | 3/1994 | Pohl et al. ..................... 502/232 |
| 5,345,005 A | 9/1994 | Thakur et al. |
| 5,977,010 A * | 11/1999 | Roberts et al. ................ 502/244 |
| 6,049,008 A | 4/2000 | Roberts et al. |
| 6,992,037 B2 | 1/2006 | Chen et al. |
| 7,465,839 B2 | 12/2008 | Ladebeck |
| 2012/0264976 A1 * | 10/2012 | Harada et al. ................. 564/420 |

* cited by examiner

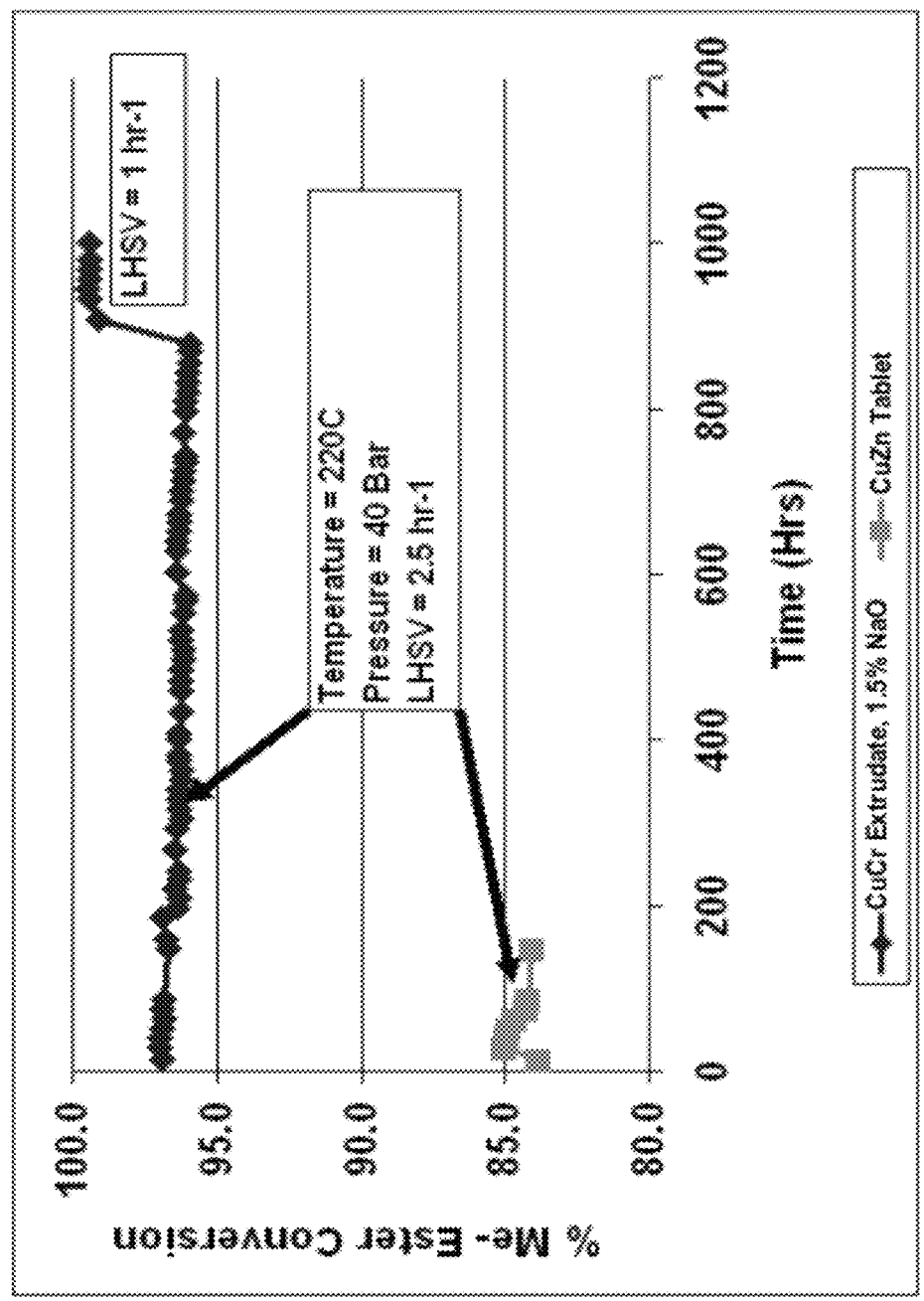

COPPER CHROMITE HYDROGENATION CATALYSTS FOR PRODUCTION OF FATTY ALCOHOLS

CROSS-REFERENCE TO RELATED APPLICATIONS

This application claims priority under 35 U.S.C. §119(e) to U.S. Patent Application Ser. No. 61/418,063, filed Nov. 30, 2010, which is incorporated herein by reference in its entirety.

TECHNICAL FIELD

This invention relates to catalysts that are particularly useful as hydrogenation catalysts, and more particularly, catalysts that are useful for hydrogenating carboxylic esters to form fatty alcohols. The invention also relates to a method of preparing these catalysts and to the use of the catalysts in hydrogenation reactions.

BACKGROUND

Hydrogenation is a chemical reaction that involves the addition of hydrogen ($H_2$) and is used in large scale industrial processes or smaller scale laboratory procedures. Copper is a known catalyst for hydrogenation reactions, and, the form that copper is provided in can impact activity and selectivity of such a catalyst. U.S. Pat. No. 5,124,295 (Nebesh), for example, is directed to copper chromite catalysts. Methyl esters having carbon chains on the order of $C_{12}$ to $C_{18}$, as an example, can be hydrogenated to the corresponding saturated fatty alcohols according to hydrogenolysis reaction (1).

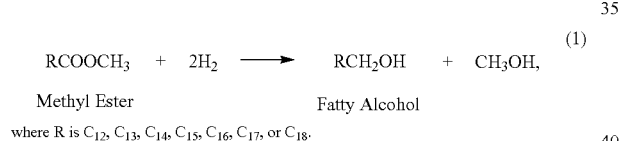

where R is $C_{12}$, $C_{13}$, $C_{14}$, $C_{15}$, $C_{16}$, $C_{17}$, or $C_{18}$.

In fixed-bed, vapor-phase fatty alcohol processes, the operating temperatures (220° C. and above) are higher than those used for the fixed-bed, liquid-phase process. The main reasons such temperatures are used are to keep the feed in gaseous phase and to avoid condensation. At these temperatures, however, endothermic reactions (reactions 2 through 4) are accelerated giving by-products such as hydrocarbons, carbonyl compounds and ethers. Reaction (2) shows dehydration of the fatty alcohol to an olefin followed by hydrogenation to a hydrocarbon. Reaction (3) shows dehydration of the fatty alcohol to an ether. Reaction (4) shows dehydrogenation of the fatty alcohol to a carbonyl compound.

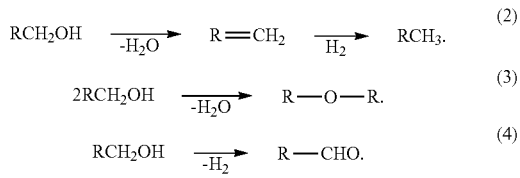

There is a continuing need to provide catalysts that maximize alcohol production while eliminating by-product formation. It is also desirable to provide hydrogenation catalysts, methods for their manufacture and methods of use, which exhibit higher catalytic activity than existing catalysts.

SUMMARY

Provided are catalysts for hydrogenation, and methods of making and using the same. The catalysts comprise a copper chromite, a mixture of a copper compound and a chromium compound; an alkali metal or alkaline earth metal component; and an inorganic matrix component; wherein the copper chromite, the alkali metal or alkaline earth metal component, and the inorganic matrix component are processed together to form the catalyst. Such catalysts have an increased selectivity for fatty alcohol as compared to a copper chromite catalyst having no alkali metal or alkaline earth metal component as used in hydrogenation reactions. One embodiment provides a catalyst formed from a blend consisting essentially of copper chromite; an alkali metal or alkaline earth metal component; and at least one an inorganic matrix component; wherein the copper chromite, the alkali metal or alkaline earth metal component, and the at least one inorganic matrix component are processed together to form the catalyst.

A method of making a catalyst for hydrogenation comprises: mixing a copper chromite powder, a combination of a copper compound and a chromium compound, or both with an inorganic matrix component to form a dry mixture; adding a solution containing an alkali metal or alkaline earth metal component to the dry mixture to form a blend; and forming the catalyst.

A method for making fatty alcohols comprises: providing a feedstock comprising a methyl ester; contacting the feedstock with one of the catalysts of the present invention; and yielding fatty alcohols.

BRIEF DESCRIPTION OF THE DRAWINGS

FIG. 1 is a graph showing % methyl-ester conversion versus time for a catalyst of the present invention and a comparison catalyst.

DETAILED DESCRIPTION

Provided are hydrogenation catalysts for processing esters into fatty alcohols. More particularly, the catalysts are for vapor-phase hydrogenation of methyl esters to fatty alcohols under fixed-bed conditions, where conditions are typically in a temperature range of 200 to 250° C. and a pressure range of 30 to 50 bar. Methods of making and using the same are also provided. These catalysts comprise a copper chromite, an alkali metal or alkaline earth metal component, and an inorganic matrix component, which are processed together to form the catalyst. Reference to "a copper chromite" means that copper chromite is present, which can be provided neat as the compound itself, or as a mixture of a copper compound and a chromium compound, or both. When provided as a mixture, without intended to be bound by theory, it is thought that the mixture forms copper chromite in situ. The alkali metal component can comprise sodium (Na), potassium (K), rubidium (Rb), caesium (Cs), or combinations thereof. Alkaline earth metals can comprise magnesium (Mg), calcium (Ca), barium (Ba), or combinations thereof.

It has been found that acidity from a feed and/or a catalyst surface can catalyze the undesirable side-reactions (2), (3), and (4) under vapor-phase, fixed-bed hydrogenation conditions. Without intending to be bound by theory, it is thought that the presence of the alkali metal component reduces acid sites on the catalyst surface, thereby, discouraging the undesirable side-reactions (2), (3), and (4) under conditions. Thus, the presence of an alkali metal, such as sodium, or of an alkaline earth metal, such as calcium, permits a higher selectivity for fatty alcohol as compared to catalysts without the alkali metal or alkaline earth metal. These catalysts are also beneficial for long life in vapor phase, fixed bed operations, where selectivity for fatty alcohol remains high even with periodic increases of temperature as the catalyst ages.

In a preferred embodiment, these catalysts contain a significant amount of mesoporosity. Reference to "mesoporosity" means those pores having a pore diameter in the range of 20 to 700 Angstroms (Å). In one or more embodiments, the catalyst has a mesopore volume of 0.20 cc/g or more and an overall pore volume of 0.25 cc/g or more. In specific embodiments, the mesopore volume is in the range of 0.20 to 0.50 cc/g, or 0.25 to 0.40 cc/g, or even 0.29 to 0.33 cc/g and an overall pore volume in the range of 0.25 to 0.60 cc/g, or 0.30 to 0.50, or even 0.35 to 0.40 cc/g. That is, the pore volume of pores having a diameter in the range of 20 to 700 Å is about 80% of the total pore volume, or more generally, in the range of about 80 to 85% of the total pore volume. Other embodiments provide that the catalyst has a surface area in the range of 30 to 80 $m^2/g$, or even 45 to 70 $m^2/g$.

All references to pore diameters and pore volumes in the specification and claims of this application are based upon measurements utilizing mercury porosimetry. A typical method is described by R. Anderson, Experimental Methods in Catalytic Research, Academic Press, New York, 1968. The pore volumes are determined utilizing the catalysts in their oxide forms. That is, the pore diameters and pore volumes reported herein are obtained for the catalyst after calcination, but prior to any reduction of the oxide. Those skilled in the art often refer to the catalyst containing the metal oxides as the "oxide" or "oxide precursor" form of the catalyst.

Catalysts will generally not contain ingredients that will affect selectivity or acidity. For example, the catalysts will not contain nickel, which could affect selectivity. Up to trace amounts of zeolites may be suitable, but not amounts that would appreciably increase acidity. As used herein the catalytic material is free of such materials if their presence is in an amount that does not materially affect the physical, chemical and catalytic characteristics of the compositions when compared to those which are completely free of such materials. Preferably, if present, such materials will be present in trace amounts, but in amounts not greater than about 0.5% by weight, more preferably not greater than 0.1% weight.

In a first aspect, provided are catalysts for hydrogenation comprising: a copper chromite; an alkali metal or alkaline earth metal component; and an inorganic matrix component; wherein the copper chromite, the alkali metal or alkaline earth metal component, and the inorganic matrix component are processed together to form the catalyst. Such catalysts have an increased selectivity for fatty alcohol as compared to a copper chromite catalyst having no alkali metal or alkaline earth component as used in hydrogenation reactions.

In one embodiment, the catalyst is prepared from a blend of: an amount of the copper chromite in the range of 60 to 90% by weight of the blend; an amount of the alkali metal or alkaline earth metal component in the range of 0.5 to 3.0% by weight of the blend; and an amount of the inorganic matrix component in the range of 10 to 40% by weight of the blend. A detailed embodiment provides a blend of 70-80 weight % copper chromite, 1.5-2.0 weight % alkali metal or alkaline earth metal component, and 20-30 weight % inorganic matrix. Another detailed embodiment provided that the catalyst is prepared from a blend of copper chromite, sodium hydroxide, silica sol, and, optionally, clay.

A detailed embodiment provides that the catalyst is effective to convert 95% or more of methyl laurate to fatty alcohol under fixed-bed conditions at 220° C., 40 bar, and an LHSV of 2.5 $hr^{-1}$ after 200 hours, or 400 hours, or 600 hours, or 800 hours, or even 950 hours.

Another aspect provides catalysts for hydrogenation formed from a blend consisting essentially of a copper chromite; an alkali metal or alkaline earth metal component; and at least one an inorganic matrix component; wherein the copper chromite, the alkali metal or alkaline earth metal component, and the at least one inorganic matrix component are processed together to form the catalyst. The blend can consist essentially of copper chromite, sodium hydroxide, silica sol, and, optionally, clay.

A further aspect is directed to a method of making a catalyst for hydrogenation comprising: mixing a copper chromite powder, a combination of a copper compound and a chromium compound, or both with an inorganic matrix component to form a dry mixture; adding a solution containing an alkali metal component to the dry mixture to form a blend; and forming the catalyst.

In yet another aspect, provided is a method for making fatty alcohols comprising: providing a feedstock comprising a methyl ester; contacting the feedstock with one of the catalysts of the present invention; and yielding fatty alcohols.

Reference to "inorganic matrix component" means a material suitable for binding components together to form a catalyst in a shape. Generally, the inorganic matrix component is extrudable and used to form extruded catalysts. Thus, the inorganic matrix component, or binder material, may be alumina, silica, zinc oxide, zirconium oxide, clay such as Bentonite or Attapulgite, zeolites or molecular sieves, silicates such as calcium silicate, etc., and mixtures thereof. In a preferred embodiment, the silica source is silica sol. Suitable clays include Attagel-30.

A preferred way to process the blend of all of the ingredients is to extrude it through a shaping orifice to form an extruded catalyst body, or extrudate. Other catalyst bodies can be shaped into spheres or any other convenient formation.

Before describing several exemplary embodiments of the invention, it is to be understood that the invention is not limited to the details of construction or process steps set forth in the description. The invention is capable of other embodiments and of being practiced or being carried out in various ways.

EXAMPLES

Example 1

A series of copper chromite catalysts having varying levels of the alkali metal sodium were prepared as follows. Copper chromite powder was dry mixed with Attagel-30 clay in a mixer. Silica sol and a sodium-containing soluble salt, sodium hydroxide, were added to the dry mix. A solution containing copper nitrate was added to these ingredients with continuous mixing to form a wet-pill mix. The wet-pill mix was extruded using an extruder. The catalysts had the following properties:

TABLE 1

|  | Example1A | Example1B | Example1C | Example1D |
|---|---|---|---|---|
| % $Na_2O$ @ 500° C. | 0.5 | 1.1 | 1.6 | 2.0 |
| Size/shape | 1/16" 3F | 1/16" 3F | 1/16" 3F | 1/16" 3F |

TABLE 1-continued

|  | Example1A | Example1B | Example1C | Example1D |
|---|---|---|---|---|
| Surface area (m$^2$/g) | 54 | 53.2 | 57.9 | 57.9 |
| Pore Volume (cc/g) | | | | |
| up to 60 Å | 0.02 | — | 0.03 | — |
| up to 90 Å | 0.03 | — | 0.04 | — |
| up to 120 Å | 0.05 | — | 0.06 | — |
| up to 350 Å | 0.32 | — | 0.31 | — |
| up to 700 Å | 0.33 | — | 0.32 | — |
| up to 1000 Å | 0.34 | — | 0.33 | — |
| up to 10000 Å | 0.35 | — | 0.37 | — |
| up to 94700 Å | 0.36 | 0.37 | 0.39 | 0.395 |
| Crush strength, lbs./mm | 2.1 | 2.42 | 2.54 | 2.54 |
| PABD, g/cc | 0.91 | 0.92 | 0.93 | 0.93 |
| % CuO @ 500° C. | 40 | 38.4 | 37.8 | 37.8 |
| % Cr$_2$O$_3$ @ 500° C. | 31 | 32.3 | 32.2 | 32.2 |
| % SiO$_2$ @ 500° C. | 19 | 20.0 | 20.0 | 20.0 |
| % MnO$_2$ @ 500° C. | 4 | 3.2 | 3.2 | 3.2 |
| % La$_2$O$_3$ | Nil | Nil | Nil | Nil |
| % Al$_2$O$_3$ | Nil | Nil | Nil | Nil |

Example 2

Testing

The copper chromite catalysts of Example 1 were tested for activity and C-12 hydrocarbon selectivity under conditions of pressure 30 bar, temperature 220° C., LHSV 2.5 hr$^{-1}$, hydrogen/feed ratio 250:1, feed of methyl ester (having a saponification value (SAP) of about 260 mg KOH/g). The catalyst yielded the following activities (as measured by SAP value) and selectivities.

TABLE 2

|  | Example 1A | Example 1B | Example 1C | Example 1D | Example 1E | Example 1F |
|---|---|---|---|---|---|---|
| % Na$_2$O @ 500° C. | 0.5 | 1.1 | 1.6 | 2.0 | 2.5 | 3.0 |
| Activity (SAP # mg KOH/g) | | | | | | |
| 8 hrs | 6.05 | 8.04 | 7.26 | 5.48 | 9.68 | 22.35 |
| 17 hrs | 5.12 | 7.90 | 7.35 | 5.87 | 9.47 | 20.86 |
| 22 hrs | 4.52 | 7.96 | 7.67 | 6.08 | 9.64 | 22.38 |
| 41 hrs | 4.29 | 7.98 | 7.85 | 6.07 | 9.45 | 23.30 |
| 46 hrs | 3.82 | 8.18 | 8.13 | 6.11 | 10.04 | 24.07 |
| 64 hrs | 4.10 | 8.14 | 8.43 | 6.18 | 9.97 | 24.88 |
| 90 hrs | 4.46 | 8.28 | 8.40 | 6.71 | 9.98 | 23.48 |
| 113 hrs | 4.06 | 8.60 | 8.55 | 6.48 | 9.92 | 23.39 |
| 118 hrs | 4.30 | 8.53 | 8.54 | — | — | 25.04 |
| 136 hrs | 3.81 | 8.09 | 8.60 | — | — | 23.95 |
| 141 hrs | 3.70 | — | 8.04 | — | — | — |
| 150 hrs | 4.19 | — | 7.90 | — | — | — |
| % C-12 hydrocarbon | | | | | | |
| T 17 hrs | 0.56 | 0.32 | 0.32 | 0.28 | 0.33 | 0.21 |
| T 22.25 hrs | 0.57 | 0.34 | 0.33 | 0.28 | 0.32 | 0.22 |
| T 40.75 hrs | 0.56 | 0.33 | 0.33 | 0.28 | 0.32 | 0.21 |
| T 45.75 hrs | 0.53 | 0.33 | 0.32 | 0.28 | 0.32 | 0.20 |
| T 64 hrs | 0.52 | 0.33 | 0.35 | 0.28 | 0.31 | 0.19 |
| T 90 hrs | 0.52 | 0.32 | 0.34 | 0.26 | 0.33 | 0.19 |
| T 112.5 hrs | 0.50 | 0.32 | 0.34 | 0.28 | 0.33 | 0.19 |
| T 118 hrs | 0.50 | 0.32 | 0.34 | 0.30 | 0.33 | 0.19 |
| T 135.75 hrs | 0.51 | 0.33 | 0.35 | 0.30 | 0.33 | 0.18 |
| T 140.75 hrs | 0.50 | — | 0.35 | — | 0.32 | 0.18 |

The data of Table 2 show that selectivity for the C-12 hydrocarbon, which is the by-product according to reaction (2) above, generally decreases as the sodium content increases. The SAP value is lowest for a sodium level of 2.0%, which indicates the highest conversion of the feed.

Example 3

Comparative

A copper chromite catalyst having no sodium was prepared as follows. Copper chromite powder was dry mixed with Attagel-30 clay in a mixer. Silica sol was added to the dry mix. A solution containing copper nitrate was added to these ingredients with continuous mixing to form a wet-pill mix. The wet-pill mix was extruded using an extruder.

Example 4

Testing

A copper chromite catalyst according to Example 1, having a Na$_2$O level of 1.5% by weight, was tested for methyl ester conversion under conditions of pressure 40 bar, temperature 220° C., hydrogen/feed 250:1, feed of fatty methyl ester. Testing occurred at LHSV 2.5 hr$^{-1}$ until just before 1000 hours, when the LHSV was increased to 1 hr$^{-1}$. A comparison CuZn tableted catalyst having no alkali metal component was tested under the same conditions until just before 200 hours. FIG. 1 shows the superior conversion of the extruded alkali component-containing catalyst as compared to the comparison catalyst.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:
1. A catalyst for hydrogenation comprising:
a copper chromite;
an alkali metal or alkaline earth metal component; and
an inorganic matrix component;
wherein the copper chromite, the alkali metal or alkaline earth metal component, and the inorganic matrix component are processed together to form the catalyst, and
wherein the alkali metal component comprises sodium (Na), potassium (K), rubidium (Rb), caesium (Cs), or combinations thereof or the alkaline earth metal comprises magnesium (Mg), calcium (Ca), or combinations thereof.

2. The catalyst of claim 1, wherein the copper chromite is provided neat, as a mixture of a copper compound and a chromium compound, or both.

3. The catalyst of claim 1 that is prepared from a blend of:
an amount of the copper chromite in the range of 60 to 90% by weight of the blend;
an amount of the alkali metal component in the range of 0.5 to 3.0% by weight of the blend; and
an amount of the inorganic matrix component in the range of 10 to 40% by weight of the blend.

4. The catalyst of claim 1 that is prepared from a blend of copper chromite, sodium hydroxide, silica sol, and, optionally, clay.

5. The catalyst of claim 1 having a mesopore volume in the range of 0.20 to 0.50 cc/g and an overall pore volume in the range of 0.25 to 0.60 cc/g.

6. The catalyst of claim 1 having a surface area in the range of 45 to 70 $m^2/g$.

7. The catalyst of claim 1 being effective to convert 95% or more of methyl laurate to fatty alcohol under fixed-bed conditions at 220° C., 40 bar, and an LHSV of 2.5 $hr^{-1}$ after 200 hours.

8. The catalyst of claim 1 having an increased selectivity for fatty alcohol as compared to a copper chromite catalyst having no alkali metal or alkaline earth metal component as used in hydrogenation reactions.

9. The catalyst of claim 8, wherein the blend consists essentially of copper chromite, sodium hydroxide, silica sol, and, optionally, clay.

10. A method of making a catalyst for hydrogenation comprising:
mixing a copper chromite powder, a combination of a copper compound and a chromium compound, or both with an inorganic matrix component to form a dry mixture;
adding a solution containing an alkali metal or alkaline earth metal component to a dry mixture to form a blend; and
of claim 1,
wherein the alkali metal component comprises sodium (Na), potassium (K), rubidum (Rb), caesium (Cs) or combinations thereof or the alkaline earth metal comprises magnesium (Mg), calcium (Ca), or combinations thereof.

11. The method of claim 10, wherein the blend comprises:
an amoind of the copper chromite in the range of 60 to 90% by weight;
an amount of the alkali metal or alkaline earth metal component in the range of 0.5 to 3.0% by weight; and
an amount of the inorganic matric component in the range of 10 to 40% by weight.

12. The method of claim 10, wherein the blend comprises copper chromite, sodium hydroxide, silica sol, and, optionally, clay.

13. A method for making fatty alcohols comprising:
providing a feedstock comprising a methyl ester;
contacting the feedstock with the catalyst of claim 1; and
yielding fatty alcohols.

14. The method of claim 13, wherein the catalyst is prepared from a blend of:
an amount of the copper chromite in the range of 60 to 90% by weight of the blend;
an amound of the alkali metal or alkaline earth metal component in the range of 0.5 to 3.0% by weight of the blend; and
an amount of the inorganic matrix component in the range of 10 to 40 % ny weight of the blend.

15. The method of claim 13, wherein the catalyst has a mesopore volume in the range of 0.20 to 0.50cc/g and an overall pore volume in the range of 0.25to 0.60cc/g.

16. The method of claim 13, wherein the catalyst has a surface area in the range of 45 to 70 $m^2/g$.

17. The method of claim 13, wherein the catalyst is effective to convert 99.5% or more methyl laurate to fatty alcohol under fixed-bed conditions at 220°C., 30 bar, and an LHSV of 2 $hr^{-1}$ after 200 hours.

18. A catalyst for hydrogenation formed from a blend consisting essentially of
a copper chromite;
an alkali metal or alkaline earth metal component; and
at least one an inorganic matrix component;
wherein the copper chromite, the alkali metal or alkaline earth metal component, and the at least one inorganic matrix component are processed together to form the catalyst, and
wherein the alkali metal component comprises sodium (Na), potassium (K), rubidium (Rb), caesium (Cs), or combinations thereof or the alkaline earth metal comprises magnesium (Mg), calcium (Ca), or combinations thereof.

* * * * *